United States Patent
Olisa, III (10) Patent No.: US 7,244,702 B2
(45) Date of Patent: Jul. 17, 2007

(54) PURIFIED CYS MOIETY FOR IRON REDUCTASE, AND METHOD FOR OBTAINING AND USING SAME

(75) Inventor: N. Robert Olisa, III, Washington, DC (US)

(73) Assignee: Nzedegwu Robert Olisa, III, El Paso, TX (US)

( * ) Notice: Subject to any disclaimer, the term of this patent is extended or adjusted under 35 U.S.C. 154(b) by 92 days.

(21) Appl. No.: 10/249,607

(22) Filed: Apr. 23, 2003

(65) Prior Publication Data

US 2004/0214998 A1  Oct. 28, 2004

(51) Int. Cl.
*C07K 14/02* (2006.01)

(52) U.S. Cl. ........................ 514/2; 530/324; 530/325; 530/326; 530/327; 514/12; 514/13; 514/14; 514/15; 436/89

(58) Field of Classification Search .................. 514/2, 514/12–16; 530/324, 325, 326, 327; 436/89
See application file for complete search history.

(56) References Cited

U.S. PATENT DOCUMENTS

| | | |
|---|---|---|
| 7,109,480 B2 * | 9/2006 | Vestal et al. ................ 250/288 |
| 7,166,441 B2 * | 1/2007 | Nadler et al. ................ 435/23 |
| 2004/0076981 A1 * | 4/2004 | Yoder et al. ................ 435/6 |

* cited by examiner

*Primary Examiner*—David Lukton (57) ABSTRACT

The invention comprises a preparation of X-S-Cys-X, moiety, BRAUNMYCIN Î>>, where X maybe naturally linked peptide or glycan residues essential for iron-reductase activity, as well as methods of obtaining preparation from an iron-nitriloacetic acid iron binding jaw, BRAUNMYCIN8567, a component of a batch affinity column; and any interpretation derived from this outcome, like, but not limited to, detection of resistance, to iron-containing antibiotics, in DNA synthesizing cells.

10 Claims, 5 Drawing Sheets

Figures

Figure 1A: POLYSTYRENE WITH LINKER

Figure 1B: BRAUNMYCINB567

* Nitilo-triacetic-acid

Figure 1C: BRAUNMYCINλ

[XDIHGLGNIKNYCPIVGSENKX] in SpibpA

[XTTVYCSNCQKXEAFDLCVRLFNQELDRPLRX] in SpibpB

[XCDVLVQQLMEEPRXTAETTCYEIFREILRXVVADCVAAEGIEGQGGFILX] in SpibpC

[X-C-X UNDETERMINED] in SpibpD

Figure 2: MALDI-TOF MS MASS FINGER PRINT, AMMINO ACID SEQUENCING AND DATABASE SEARCH ANALYSIS FOR MASS IDENTITY BRAUNMYCIN2/SpibpA (a novel peptide)

BRAUNMYCIN2/SpibpB (a novel peptide)

Figure 2: MALDI-TOF MS MASS FINGER PRINT, AMMINO ACID SEQUENCING AND DATABASE SEARCH ANALYSIS FOR MASS IDENTITY Figure 3 :  MALDI-CID MS MASS FINGER PRINT, AMMINO ACID SEQUENCING
AND DATABASE SEARCH ANALYSIS FOR MASS IDENTITY Figure 3 :   MALDI-CID MS MASS FINGER PRINT, AMMINO ACID SEQUENCING
AND DATABASE SEARCH ANALYSIS FOR MASS IDENTITY BRAUNMYCIN3/SpibpB (a novel peptide)

PURIFIED CYS MOIETY FOR IRON REDUCTASE, AND METHOD FOR OBTAINING AND USING SAME

BACKGROUND OF INVENTION

Iron (II) is an important molecule to pathogens. Iron (II) can be acquired from Iron (III), the more readily available form, by reductase activity. According to Brown et al, 2002, Rev Microbes and Infection 4(11): 1149-1156, Iron (II) can be utilized by most pathogens for the purpose growth and virulence. Previously, genetic studies by Kadner, et al, J. Bacteriol. 143:256-264. (1980), show that drug resistance, in *Escherichia coli*, to iron containing antibiotics, can result from gene mutations in its iron uptake genes.

The invention relates to a preparation comprising X-S-Cys-X peptide moiety, hereon referred to as BRAUNMYCINÎ>>, (where Î>> is equal to X-S-Cys-X.) for iron-reductase activity; and methods of obtaining purified iron-binding, iron-reductase, moiety, using a iron-nitriloacetic acid jaw, $Fe^{3+\ or\ 2+}$-NTA, IBPJAW, hereon, referred to as BRAUNMYCIN8567, as an accessory, in batch affinity chromatography; and the interpretation of this activity, like its use in detecting resistance to iron-containing antibiotics in Deoxyribonucleic acid, or DNA, producing cells. X, as used above, maybe either or both of glycan sugars, or peptide sequences >0.12 kDa in length.

The present invention was developed from studies utilizing genetic information on pneumococcal genetic sequences relating to iron acquisition genes previously made public through the NCBI gene Bank database, under gene accession number AF338658.1; GI 18478640 at http://www.tigr.org (2002), by Olisa, N. R., et al, reported earlier In Abstracts of The 100th General Meeting of the American Society for Microbiology B-22, p.45 (2000) by the same author. The present invention, has been developed to function as an accessory in batch affinity chromatography.

The present invention was evaluated using a *Streptococcus pneumoniae* wild type Rx1 strain, a spontaneous albomycin resistant strain alb⁻, isolated from Rx1, and a genetically induced albomycin resistant strain, created as a result of the reverse genetics of a major pneumococcal iron acquisition gene, pia⁻in Rx1. The choice of *S. pneumoniae* as a model, stems from the fact that the organism in question displays a scrupulous need for iron (II). According to studies performed by Tai et al, 1993, Infect. Immun. 61:5401-1087, *S. pneumoniae* lack siderophore. Based on this information, theoretically, they should have well-developed cell wall iron-reductase for use in iron acquisition.

The present invention was used to purify unique X-S-Cys-X peptides from cell wall iron-reductase in Rx1. The inability of the present invention to purify same sequences in mutant strains, formed the scientific basis for detecting albomycin resistance in alb⁻, and pia⁻ mutants. Albomycin, is an iron-containing antibiotic, and natural siderophore produced by *Streptomyces* spp. In example, we use albomycin, as a marker, for iron-reductase activity, since killing by the antibiotic occurs when iron present in its molecules are reduced or taken up.

The uniqueness of the present invention was determined after extensive databases searches in the achieves of the US patent and trademark office, using the key words iron-reductase, and iron-nitriloacetic acid. When iron-reductase was used in search, results yielded a single insignificant match. It appears that Zenno et al, 1995, was awarded a U.S. Pat. No. 5,468,631 for a gene encoding an enzyme, flavin, with reducing activity and nitroreductase activity. This gene, the enzyme, as well as their techniques are unrelated to ours.

The pure form of the functional X-S-Cys-X moiety from iron-reductase, targeted by our preparation, may or may not contain glycan sugars. Furthermore, our technique is not genetic, it is a batch affinity protocol, and computational proteomics that uses, a unique JAW to capture glycan sugar containing peptides of the S-Cys, mass spectrometry sequencing, and database searches. Finally, in reference to the database search, there were no matches using the key word iron-nitriloacetic acid.

SUMMARY OF INVENTION

The invention, $Fe^{3+\ or\ 2+}$-NTA, IBPJAW or BRAUNMYCIN8567, a synthetic siderophore, is a low molecular weight iron chelator, that can be used in a batch affinity chromatography to purify the invention component, a preparation consisting of X-S-Cys-X peptide moiety, or BRAUNMYCIN Î>> from iron-reductase. For this to occur, the invention has to be anchored or linked to a larger molecule, like polystyrene. The present invention specifically targets S-Cys, an amino acid. Since this amino acid is identical, regardless of cell, the invention can be used to isolate, and purify S-Cys in any DNA containing, and functioning iron-reductase(s), regardless of cell type. All living cells use DNA for the synthesis of S-Cys. When S-Cys moiety is deficient of hydrophilic, or other reactive amino acids, the targeted iron-binding proteins will not be purified, since the properties of the S-Cys moiety will not reduce iron present in the synthetic siderophore, $Fe^{3+\ or\ 2+}$-NTA, IBPJAW or BRAUNMYCIN8567. In principal, this forms the basis for the use of the present invention, in the detection of antibiotic resistance to naturally produced siderophores, like Albomycin, an iron-containing antibiotic, produced by *Streptomyces* spp.

There are many ion exchange columns in existence like $Ni^{2+}$-NTA. Their function is dependent on the ionic charge present in target. Conversely, $Fe^{3+/2}+$ affinity columns, if any, are rare. $Fe^{3+\ or\ 2+}$-NTA IBPJAW or BRAUNMYCIN8567 was designed to be artificially identical in structure to iron complexes that are naturally present in humans like hemoglobin, hemoprotiens, transferring and lactoferrin; and functionally similar to naturally occurring siderophores. The bonds in the $Fe^{3+\ or\ 2+}$-NTA, IBPJAW or BRAUNMYCIN8567 are identical to those of $Fe^{3+\ or\ 2+}$ found in most human cells like Hemoglobin, transferring, and lactoferrin.

In nature, it would take a reductase activity to remove iron bound to either of these molecules. At present, existing batch affinity columns, and ion exchange columns, do not function on a reduction mode, a critical, physiologic process and unique feature of the $Fe^{3+\ or\ 2+}$-NTA, IBPJAW or BRAUNMYCIN8567. To ensure we purify iron-reductase, we linked $Fe^{3+\ or\ 2+}$ to NTA. In doing so, we created a JAW that uses six oxygen atoms to engage $Fe^{3+\ or\ 2+}$. This arrangement binds iron in the jaw in all six coordination sites. In addition, to prevent $Fe^{3+\ or\ 2+}$-NTA, or BRAUNMYCIN8567 from being internalized or absorbed by cell or substrate, we linked or anchored Fe $Fe^{3+\ or\ 2+}$-NTA IBPJAW or BRAUNMYCIN8567 to polystyrene, a relatively larger matrix. This unique feature allows for affinity purification of peptides that target and bind $Fe^{3+\ or\ 2+}$-NTA IBPJAW or BRAUNMYCIN8567.

At present, most ion columns bind in four, of six available coordination sites, freeing two sites for activity, a practice that reduces binding and purification specificity for iron-reductase. Conversely, by binding all six coordination sites, the present invention has the major advantage of increased specificity, and sensitivity in the purification of iron-binding proteins. Specifically, iron-binding protein reductase.

BRIEF DESCRIPTION OF DRAWINGS

FIG. 1C refers to two key points. Firstly, to a component of invention, a preparation called BRAUNMYCIN Î>>, or X-S-Cys-X moiety, purified from cell wall extracts containing MALDI-TOF MS and MALDI-CID MS deduced cysteine containing amino acid sequences of S. pneumoniae iron-binding proteins, Spibp, from Rx1 strain of S. pneumoniae after affinity chromatography using $Fe^{3+ \ or \ 2+}$-NTA IBPJAW or BRAUNMYCIN8567. Secondly, FIG. 1C shows a 4-14% sodium dodecyl sulfate polyacrylamide gel after the electrophoresis. The gel depicts an interpretation that can be drawn from non-binding activity in two other mutant strains of Rx1: a spontaneous albomycin, or iron-containing antibiotics, resistant strain, alb-, derived from Rx1; and a laboratory-engineered pia-, pneumococcal iron acquisition gene.

FIG. 2A, B, C, D refers to the mass fingerprints of Spibp A, B, C, D, from cell wall extracts from Rx1 using Matrix-Assisted Laser Desorbtion Ionization Time of Flight Mass Spectrophotometer (MALDI-TOF MS). In at least one case, that of 40 kDa SpibpC, MS-tag database searches was conducted using MALDI-PSD, to determine probable cysteine amino acid sequence. (all measurement are approximately Â±3)

FIGS. 3A, B, and C refer to a spectrum of 2.2 kDa peptide of the 66 kDa SpibpA fragment; and 1.25 kDa, 2.39 kDa peptides from the 50-kDa SpibpB fragments generated using Matrix-Assisted Laser Deabsorbtion Ionization Collision-Induced Dissociation Mass Spectrophotometer (MALDI-CID MS). The sequences deduced from databases by computational Proteomics are also displayed above each spectrum. (All measurement are approximately Â±3)

DETAILED DESCRIPTION

By definition, a siderophore is a low molecular weight ferric chelator produced, and secreted by microorganisms. By BRAUNMYCIN8567 is meant a component of present invention, a synthetic siderophore, made under laboratory conditions.

The present invention can be mounted on larger particles like polystyrene, and used in batch affinity chromatography, to purify BRAUNMYCIN Î>> or X-S-Cys-X peptide moiety residues, a preparation and component of invention. Synthesis of $Fe^{3+ \ or \ 2+}$-NTA, IBPJAW or BRAUNMYCIN8567.

The anchor, polystyrene, was easily obtained commercially with attached linkers (Xenopore, N.J., USA). Nitriloacetic acid, (F. Hoffmann La Roache, Germany) or NTA was linked directly to polystyrene by immersing NTA in a solution of chelate and water overnight. Afterwards, the covalently linked beads was washed extensively to remove unbound material. Coating of $Fe^{3+ \ or \ 2+}$ to NTA, covalently cross-linked to polystyrene, was formed in neutral pH buffer using 0.05 M PBS at a pH of 7.4. With 1% of ferric chloride ($Fe^{+++}$), or iron sulphate ($Fe^{++}$). Mixture can be soaked for one hour at room temperature.

Once synthesized, there are approximately $10^{13}$ per square centimeter of iron binding sites per square centimeter of surface area in a 91-106 microns polystyrene bead. And about 0.6 square centimeters per milligram of particle, this results in a concentration of approximately $10^{-8}$ moles of iron per gram of bead.

Figure 1A:
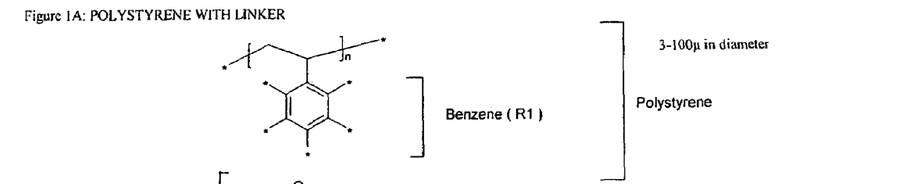
FIG. 1A refer to a drawing of a 3 to 100 microns batch affinity polystyrene bead, which can be used to anchor the invention during batch affinity chromatography.
Figure 1B:
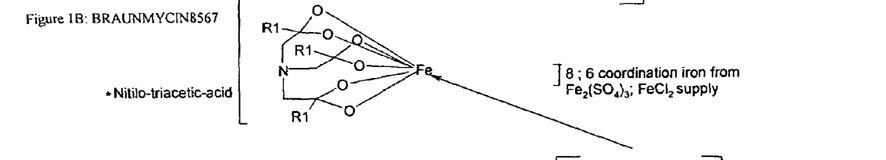
FIG. 1B refer to the invention, a drawing of $Fe^{3+ \ or \ 2+}$-NTA IBPJAW, or BRAUNMYCIN8567. Here, iron (II and III) is bound to Nitriloacetic acid, in all six coordination sites to form an iron jaw.

In reference to FIG. 1B, when complexed, the $Fe^{3+ \ or \ 2+}$-NTA jaw or BRAUNMYCIN8567 has a molecular weight of 250.01, and an exact mass of 250. The molecular formula is $C_6H_{12}FeNO_6$. The molecular composition is C 28.83%, H 4.84%, Fe 22.34%, N 5.60%, and O 38.40%. Purification of X-S-Cys-X moiety residues or BRAUNMYCIN Î>>.

The present invention was used to purify one of its components, BRAUNMYCIN Î>>(where Î>> is equal to X-S-Cys-X.) essential for iron-reductase activity. The process involves a batch affinity protocol using cell extracts of interest. Generally, the cell in question should be DNA producing, in order for it posses S-Cys, a target of the assay. The affinity column is characterized by an iron-nitriloacetic acid $Fe^{3+ \ or \ 2+}$-NTA, IBPJAW, or BRAUNMYCIN8567— the invention, was anchored to a larger molecule like polystyrene an accessory. Identification of BRAUNMYCIN Î>>.

Figure 1C:
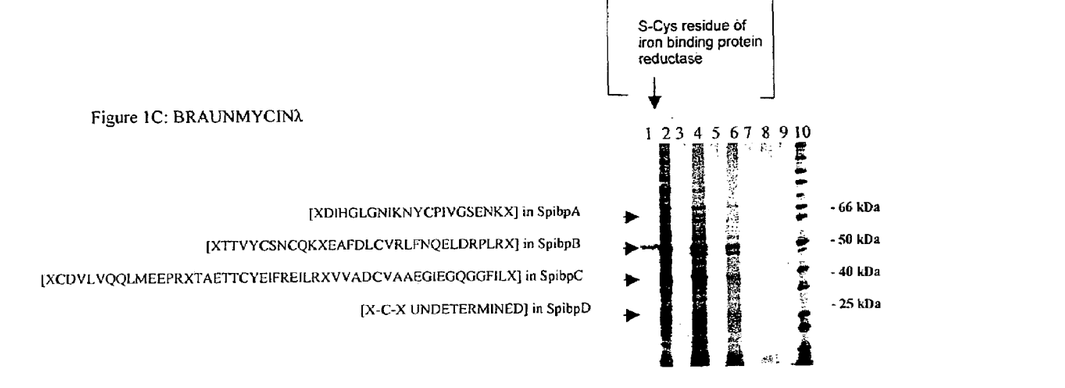
Figure 2:
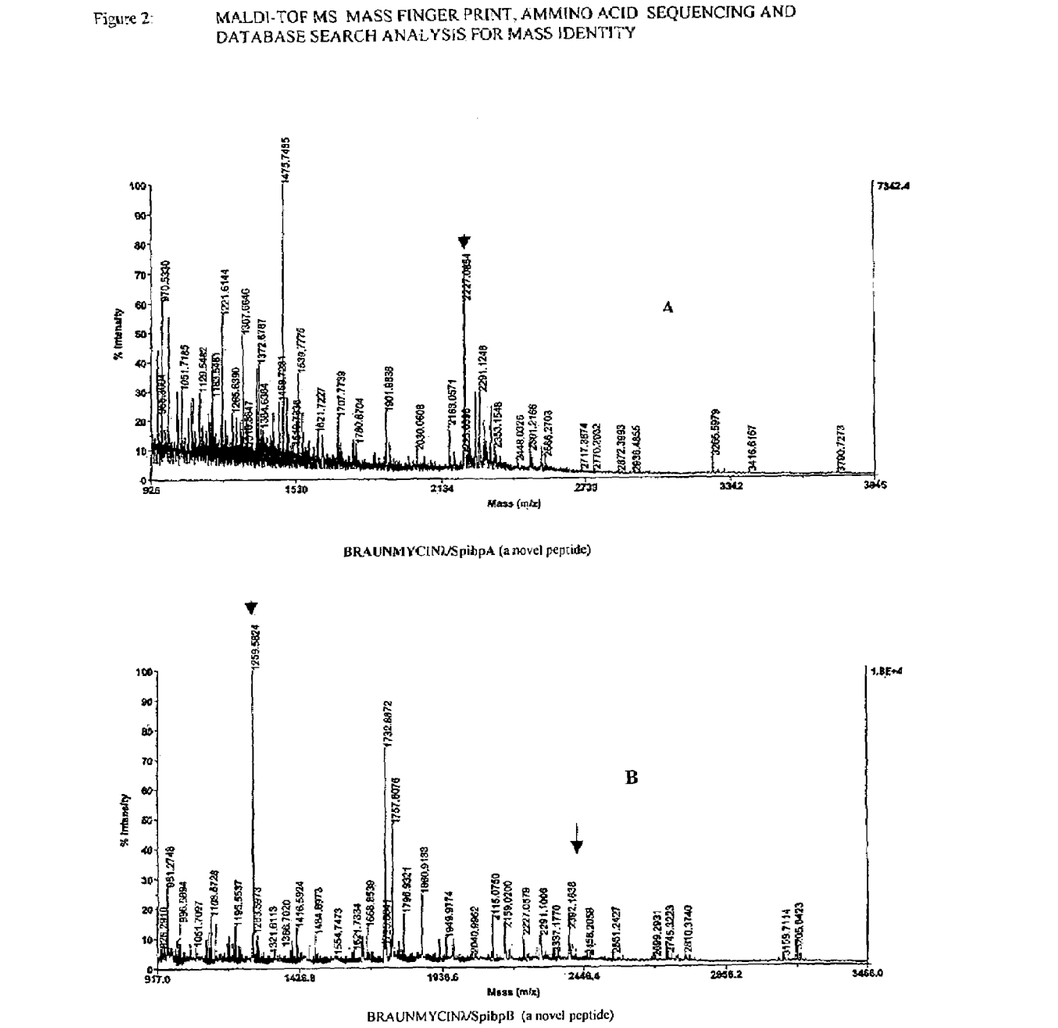
Figure 3:
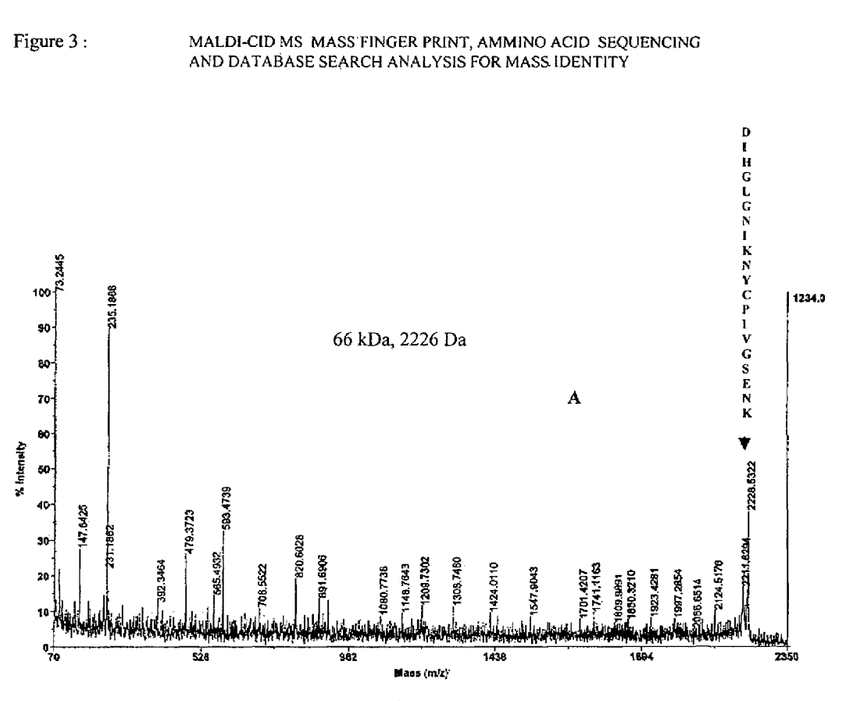

In reference to FIG. 1C, purified, form of elute, BRAUNMYCIN Î>>, is >0.121 kDa in size. The actual size depends on X, were X is any peptide or glycan molecule naturally linked to the S-Cys (pk 8.5), and purified by the preparation. Computational Proteomics was used. After MALDI-TOF MS/MALDI-CID MS, short peptides in spectrum were screened for Cysteine containing fragments. Homology searches of these fragments were performed on scientific databases that house genome sequence. Identified sequences were then characterized.

Interpretation of Binding Activity of BRAUNMYCIN Î>> to BRAUMYCIN8567.

In the present invention, binding activity in the preparation can be defined as the any partial substitution of oxygen iron (O—Fe) bonds in BRAUNMYCIN8567 with new sulfur (S) bonds present in BRAUNMYCIN Î>> to form new sulfur iron bonds (S—Fe). Conversely, non-binding refers to the absence, or significantly reduced S—Fe bonds in the preparation. For instance, non-binding activity to BRAUNMYCIN8567, in preparation, can be interpreted as resistance to albomycin, a natural siderophore with antibiotic properties due to a hydrophobic or absent X-S-Cys-X moiety.

EXAMPLES

The invention is illustrated further by the following examples, which are not to be construed as limiting the invention in scope, or spirit to the specific compounds or procedures described in them, or in any other way limiting the inventions scope.

Example 1

This example details how desired strains were collected.

S. pneumoniae strains, are readily available from clinical isolates in hospitals, as well as from the American Type Culture Collection, ATCC. Spontaneous albomycin resistant mutant strains can be isolated from wild type strains using the Kirby Bauer disk diffusion antimicrobial susceptibility assay techniques off a Muller Hinton Blood Agar. Mutant strains can be spotted growing in a zone of inhibition.

Albomycin can be readily purchased in most European biotechnology companies and universities.

Example 2

Deferralation of Media.

This example describes methods for removing iron in growth media, in order to create low iron environmental conditions needed for cells to genetically express cell wall iron-reductase.

To remove deferralated growth media, one-third strength THB was mixed with 20 g per liter of chelex resins (Bio-Rad, Hercules, Calif.) for 24 hours at 4° C. The treated medium was cleared of resins by filtration before use. Removal of iron limited the growth of organism. To rescue the growth, different iron sources was added as indicated. Plasticware or acid-washed glassware was used throughout the experiments.

Example 3

Construction and Isolation of $pia^-$ and Spontaneous resistant, Rx1, strain, $alb^-$.

Standard Kirby Bauer antimicrobial susceptibility assay was performed using Rx1 on Muller Hinton Blood Agar plates. Spontaneous mutants were isolated from zones of inhibition after incubation at 37° C. for 18 hours.

Example 4

Extraction of cell wall iron-binding protein reductase.

This example describes the preparation of a crude cell wall extract containing cell wall iron-reductase of *Streptococcus pneumoniae.*

Pneumococal cell wall iron-reductase were extracted by growing 5 ml overnight cells in 40 ml Chelex-100 treated THB agar, after initially supplementing with 5 ml of solution A (10 Î¼M $Cu^{++}$, 10 Î¼M $Zn^{++}$, 100Î¼M $Mn^{++}$, 100 Î¼M $Ca^{++}$, and 1 mM $Mg^{++}$). 50 ml late log phase cells were pelleted by centrifugation at 4000×g for 10 minutes, and washed twice in solution B (10 mM phosphate buffered saline, PBS, pH 7.4). Pelleted cells were adjusted to an Absorbance of $A_{600}$ before 0.6 mldigestion buffer, or solution C (20% wt/vol sucrose, 30% wt/vol raffinose, 50 mM $MgCl_2$ 1 mg benzamidine per ml, 0.5 mg phenylmethylsulfonyl fluoride per ml in 10 ml Tris HCl pH.7.4) was added. Mixture was incubated for 12 to 23 hours at room temperature. Protoplasts were removed by centrifuged at 1,200×g for 5 minutes. Supernatant containing cell wall iron-reductase extract was collected and stored at 20° C. prior to electrophoresis.

The crude cell wall extract will contain a number of other cell wall metal binding and iron binding proteins.

Example 5

Purification of cell-wall iron-binding protein reductase.

This example describes the purification of cell wall iron-reductase from crude cell wall extract of *S. pneumoniae.*

To purify cell wall iron-reductase, 600 ¼ g of sample from example 4, was incubated with 50 µl Fe sup.3+ or 2+NTA "IBPJAW" or BRAUNMYCIN8567 (that has been covalently linked to polystyrene).

Example 6

Separation of purified BRAUNMYCIN Î>> containing iron-binding proteins.

This examples describes methods to separated and unfold purified cell wall iron-reductase obtained in example 5 using Gel Electrophoresis.

To further isolate pure forms of iron-reductase and to determine molecular weight of sample purified in example 5, the preparation used sodium dodecyl sulphate polyacrylamide gel ectrophoresis, SDS PAGE, with 4 to 14% gradient gels. 3 µ of affinity-purified protein previously mixed in standard SDS PAGE sample buffer, was pre-heated to 70.degree. C. for 10 min.

In reference to FIG. 1C, Lane 1, show $Fe^{3+\ or\ 2+}$-NTA column extract containing 66, 50, 40, and 25 kDa, peptide reductase isolated from *S. pneumoniae* Rx1, iron binding proteins, Spibp; lane 2: show crude wall extract from Rx1; lane 3: $Fe^{3+\ or\ 2+}$-NTA column extract showing no purification from $alb^-$, cell wall; lane 4: showing crude cell wall extract from $alb^-$; lane 5: $Fe^{3+\ or\ 2+}$-NTA column extract showing no purification from $pia^-$ cell wall; lane 6: crude cell wall extract from $pia^-$; lane 8: $Fe^{3+\ or\ 2+}$-NTA column extract showing weak purification in positive control, an iron (II) saturated cell wall extract of Rx1; lane 9: naked polystyrene (no $Fe^{3+\ or\ 2+}$-NTA JAW) column extract showing no purification in negative control, a cell wall extract of Rx1. (all measurements are approximately Â±3)

Example 7

Identification of X-S-Cys-X peptide moiety, BRAUNMYCIN Î>>, from purified iron-binding reductase.

This example describes methods of identifying BRAUNMYCIN Î>> in purified cell wall iron-reductase using Mass Spectrometry.

To create polypeptides, sample in example 6 were digested with trypsin. Purified and isolated protein was cut out of a 4 to 14% gradient SDS PAGE gel, and placed in siliconized microcentrifuge tubes. The gel was destained with and dehydrated by washing three times for 10 min with 25 mM $NH_4HCO$ and 50% acetonitrile, until Coomasie stain was no longer detectable. The destained particles were dried under a vacuum for 30 min. After rehydration with 25 mM $NH_4HCO$ and 0.1 Î¼ g trypsin per Î¼ l, the protein was digested overnight at 37° C. Recovery of the peptides was accomplished by extracting the digestion mixture three times with 50% acetonitrile 5% trifluroacetic acid. The amount of volatile salts present was reduced by concentrating recovered peptides in a speed vacuum centrifuge to a final volume of 5 Î¼ l. and rehydrating three times.

Matrix-Assisted Laser Desorbtion Ionization Time of Flight Mass Spectrophotometer (MALDI-TOF MS) was used to analyze unseperated trypsin digests, for the determination of molecular mass and relative abundance. Approximately {fraction (1/10)}.sup.th unseperated tryptic digestion mixture from trypsin digest were mixed at a 1:1 ratio with. α-cyano-4-hydroxycinnamic acid matrix (Hewlett-Packard) and analyzed on a ToFSpec SE MALDI TOF Mass spectrometer, MS, (Micromass Inc. Manchester, UK) with a nitrogen laser operated with a reflectron mode. Post Source Decay (PSD) sequencing was performed by varying the reflectron voltage in 9 to 11 steps, with the voltage at each step being reduced at 75% of that at the previous step. Switching the segments from individual segments together produced the entire PSD spectrum. Fragment ions from standard peptides of adrenocorticotrophic hormone was used to calibration of the PSD mode. Matrix-Assisted Laser Deabsorbtion Ionization Collision-Induced Dissociation Mass Spectrophotometer (MALDI-CIID MS) was used to sequence peptides after MALDI-TOF MS analysis. 1 μl of $\frac{1}{10}^{th}$ unseperated digestion mixture was mixed at a 1:1 ratio in a saturated solution of 2,5, dihydroxybenzenoic acid in acetone (Aldrich). Samples were analyzed by collision-induced dissociation (CID) on a mass autospec orthogonal acceleration TOF mass spectrometer (Micrmass Inc) fitted with an N.sub.2 laser (337 nm).

Proteomics was used to determine protein homology for peptides containing Cysteine amino acid residues. Blast searches in genetic databases were conducted at www.ncbi.nlm.nih.gov. The program was available over the Internet. Fragment ion mass generated by MALDI PSD or CID MS was used to search the databases for matches to peptides containing Cysteine using MS-tag. The following parameters were used in the searches: *Streptococcus* species, protein molecular mass range from 1000 to 120,000 Da. Trypsin digest, (one missed cleavage allowed), parent ion mass tolerance of Â±1.5 Da. Fragment ion mass tolerance of Â±1.5 Da. And allowanced fragment ion types a, b, y, a-$NH_3$, b-$NH_3$, $_y$—$NH_3$, and b-$H_2O$, internal. The protein sequences deduced were used to search databases for homologous proteins with NCBI"s basic local alignment search tool (BLAST).

In reference to FIG. 1 D, sequence and homologue results were determined for 25, 40, 50, and 66-kDa cell wall iron-binding, iron-reductase of *S. pneumoniae*. (All measurements are approximate Â±3).

---

What is claimed is:

1. A method of obtaining a composition comprising cysteine-containing peptides, said method comprising:
   a) obtaining cell wall iron reductase from a pathogenic, DNA-producing microorganism;
   b) contacting the iron reductase with NTA (nitrilotriacetic acid)-bearing polystyrene beads in the presence of ferric or ferrous ion for a time and under conditions effective to bind said iron reductase with the polystyrene beads;
   c) removing any unbound proteins from the NTA-bearing polystyrene beads;
   d) separating the polystyrene beads from the proteins that are bound thereto;
   e) contacting the proteins of step (d) with trypsin for a time and under conditions effective to generate peptide fragments; and
   f) isolating the peptide fragments of step (e) that contain cysteine.

2. A method of identifying cysteine-containing peptide fragments produced by tryptic digestion of iron reductase from a pathogenic, DNA-producing microorganism, said method comprising:
   a) obtaining cell wall iron reductase from a pathogenic, DNA-producing microorganism;
   b) contacting the iron reductase with NTA (nitrilotriacetic acid)-bearing polystyrene beads in the presence of ferric or ferrous ion for a time and under conditions effective to bind said iron reductase with the polystyrene beads;
   c) removing any unbound proteins from the NTA-bearing polystyrene beads;
   d) separating the polystyrene beads from the proteins that are bound thereto;
   e) contacting the proteins of step (d) with trypsin for a time and under conditions effective to generate peptide fragments;
   f) selecting a peptide fragment from step (e) that contains cysteine; and
   g) determining the amino acid sequence of the peptide fragment of step (f) using Matrix-Assisted Laser Desorption Ionization Time-of-Fight Mass Spectrometry and Matrix-Assisted Laser Desorption Ionization Collision-induced Dissociation Mass Spectrometry.

3. The method of claim 1, wherein said composition contains one or more peptide(s) selected from the group consisting of SEQ ID NOS: 1, 2, 3, and 4.

4. The method of claim 2, wherein said peptide fragment is selected from the group consisting of SEQ ID NOS: 1, 2, 3, and 4.

5. The method of claim 1, wherein said NTA-bearing polystyrene beads are present in a chromatography column.

6. The method of claim 5, wherein said separating step is achieved by eluting the chromatography column with an imidazole-containing solution.

7. The method of claim 1, step (b), wherein the iron reductase is incubated with the NTA-bearing polystyrene beads for 12-24 hours in the presence of 10 mM phosphate-buffered saline.

8. The method of claim 1, wherein said polystyrene beads have a diameter within the range of 3-100 microns, and wherein the surface of said beads comprise $10^{13}$ iron binding sites per square centimeter.

9. The method of claim 1 wherein said pathogenic, DNA-producing microorganism is *streptococcus pneumoniae*.

10. The method of claim 9 wherein said *streptococcus pneumoniae* is an albomycin-resistant mutant.

* * * * *

SEQUENCE LISTING

```
<160> NUMBER OF SEQ ID NOS: 6

<210> SEQ ID NO 1
<211> LENGTH: 20
<212> TYPE: PRT
<213> ORGANISM: Streptococcus pneumoniae

<400> SEQUENCE: 1

Asp Ile His Gly Leu Gly Asn Ile Lys Asn Tyr Cys Pro Ile Val Gly
1               5                   10                  15

Ser Glu Asn Lys
            20

<210> SEQ ID NO 2
<211> LENGTH: 10
<212> TYPE: PRT
<213> ORGANISM: Streptococcus pneumoniae

<400> SEQUENCE: 2

Thr Thr Val Tyr Cys Ser Asn Cys Gln Lys
1               5                   10

<210> SEQ ID NO 3
<211> LENGTH: 19
<212> TYPE: PRT
<213> ORGANISM: Streptococcus pneumoniae

<400> SEQUENCE: 3

Glu Ala Phe Asp Leu Cys Val Arg Leu Phe Asn Gln Glu Leu Asp Arg
1               5                   10                  15

Pro Leu Arg

<210> SEQ ID NO 4
<211> LENGTH: 13
<212> TYPE: PRT
<213> ORGANISM: Streptococcus pneumoniae

<400> SEQUENCE: 4

Cys Asp Val Leu Val Gln Gln Leu Met Glu Glu Pro Arg
1               5                   10

<210> SEQ ID NO 5
<211> LENGTH: 15
<212> TYPE: PRT
<213> ORGANISM: Streptococcus pneumoniae
```

-continued

```
<400> SEQUENCE: 5

Thr Ala Glu Thr Thr Cys Tyr Glu Ile Phe Arg Glu Ile Leu Arg
1               5                   10                  15

<210> SEQ ID NO 6
<211> LENGTH: 19
<212> TYPE: PRT
<213> ORGANISM: Streptococcus pneumoniae

<400> SEQUENCE: 6

Val Val Ala Asp Cys Val Ala Ala Glu Gly Ile Glu Gly Gln Gly Gly
1               5                   10                  15

Phe Ile Leu
```